United States Patent [19]

Kollmeyer

[11] 4,439,225
[45] Mar. 27, 1984

[54] HERBICIDAL CYANO-TETRAHYDROFURANYLMETHYL ETHER AND CYANO-TETRAHYDROPYRANYLMETHYL ETHER DERIVATIVES

[75] Inventor: Willy D. Kollmeyer, Modesto, Calif.

[73] Assignee: Shell Oil Company, Houston, Tex.

[21] Appl. No.: 388,048

[22] Filed: Jun. 14, 1982

[51] Int. Cl.³ .................... A01N 43/06; C07D 307/24
[52] U.S. Cl. ............................. 71/88; 71/92; 71/94; 544/238; 544/332; 544/336; 546/283; 549/414; 549/426; 549/472; 549/474
[58] Field of Search ............... 549/414, 426, 472, 474; 546/283; 544/238, 332, 336; 71/88, 92, 94

[56] References Cited

U.S. PATENT DOCUMENTS

| Re. 30,574 | 4/1981 | Barker et al. | 71/88 |
| 4,116,669 | 9/1978 | Barker et al. | 71/88 |
| 4,146,384 | 3/1979 | Schmidt | 71/88 |
| 4,289,884 | 9/1981 | Barker | 546/283 |

FOREIGN PATENT DOCUMENTS

| 2 | 12/1978 | European Pat. Off. |
| 13581 | 7/1980 | European Pat. Off. |
| 2724675 | 12/1978 | Fed. Rep. of Germany |

*Primary Examiner*—John M. Ford
*Assistant Examiner*—Bernard Dentz

[57] ABSTRACT

Compounds of the formula

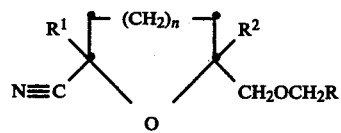

wherein $R^1$ and $R^2$ are H or alkyl; n is 0 or 1 and R is an unsaturated moiety, are useful as herbicides and plant growth regulators.

10 Claims, No Drawings

HERBICIDAL CYANO-TETRAHYDROFURANYLMETHYL ETHER AND CYANO-TETRAHYDROPYRANYLMETHYL ETHER DERIVATIVES

BACKGROUND OF THE INVENTION

1. Field of the Invention

The present invention relates to novel cyano derivatives, their use as plant growth regulators and herbicides and to compositions containing the cyano derivatives.

2. Description of the Prior Art

U.S. Pat. Nos. 4,116,669, 4,289,884 and European patent 00,002 disclose certain tetrahydrofuran derivatives useful as herbicides. German Pat. No. 2,937,645 discloses certain tetrahydropyran derivatives useful as herbicides.

Applicant has discovered a new class of herbicides and plant growth regulators in which all the compounds are characterized by the presence of a cyano group, a feature absent in the compounds of the above patents.

SUMMARY OF THE INVENTION

The present invention is directed to a compound of formula I

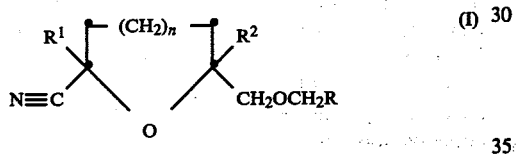

wherein $R^1$ and $R^2$ each independently is a hydrogen atom or an alkyl group containing 1 to 6 carbon atoms; n is 0 or 1; and R is an alkenyl or alkynyl group containing 2 to 4 carbon atoms; a 2-pyridinyl group; a 2-pyridazinyl group; a pyrazinyl group; a pyrimidinyl group; a 2-furanyl group; or a phenyl group optionally substituted by one or more of halogen, cyano, amino, or an alkoxy or alkylthio group containing 1 to 3 carbon atoms each optionally substituted by one or more halogen atoms having an atomic number of 9 or 17, or by an alkyl group containing 1 or 2 carbon atoms optionally substituted by one or more halogen atoms having an atomic number of 9 to 17, hydroxy, or alkoxy or alkylthio containing 1 2 carbon atoms. The compounds are useful as herbicides and to control the growth of plants.

In the compounds of formula I, $R^1$ and $R^2$ preferably contain 1 or 2 carbon atoms, i.e. methyl or ethyl. $R^1$ is preferably a methyl group. $R^2$ is preferably an ethyl group.

R is preferably an ethynyl group; a 2-pyridinyl group or a phenyl group optionally substituted by 1 or 2 chlorine or fluorine atoms or methyl groups. Three preferred subclasses of the invention are when R is 2-chlorophenyl, 2-methylphenyl and 2-fluorophenyl.

A preferred subclass of the invention is when n is 0.

Compounds that possess substantially the same plant growth regulator or herbicidal utility as those described above and can be prepared in like manner are equivalents thereof and include compounds wherein, for example, R is an unsaturated, aromatic or heteroaromatic moiety, or cyclopropyl or 1-methylcyclopropyl, including but not limited to cyano, naphthyl, imidazolyl, triazolyl, thiadiazolyl, 2-quinolinyl, 1-isoquinolinyl, pyrrolyl, cyclohexenyl, N-methylimidazolyl, N-methylpyrazolyl, isoxazoly, oxazolyl, isothiazolyl, thiazolyl, thienyl, 5-methyl-2-furanyl, and the like.

The tetrahydrofuran derivative according to the invention can exist in several geometric forms, such as cis-configuration, trans-configuration and E and Z configuration as well as in optically-active forms. These individual forms as well as mixtures thereof are within the scope of the present invention. The various isomers of the tetrahydrofuran derivatives of the invention may have different herbicidal or plant growth regulator properties. Thus, one may prefer to resolve an isomer mixture to recover a more active isomer form or to prepare the more active form directly for use in the invention.

Non-limiting species of the invention of compounds of formula I include:

Tetrahydro-2-methyl-5-ethyl-5-[(2,6-dichlorophenylmethoxy)methyl]-2-furancarbonitrile,
Tetrahydro-2-methyl-5-ethyl-5-[(2-chloro-6-fluorophenylmethoxy)methyl]-2-furancarbonitrile,
Tetrahydro-2-methyl-5-ethyl-5-[(2-(trifluoromethyl)-phenylmethoxy)methyl]-2-furancarbonitrile,
Tetrahydro-2-methyl-5-ethyl-5-[(2-methoxyphenylmethoxy)methyl]-2-furancarbonitrile,
Tetrahydro-2-methyl-5-ethyl-5-[(2-(methylthio)-phenylmethoxy)methyl]-2-furancarbonitrile,
Tetrahydro-2-methyl-5-ethyl-5-[(2,6-difluorophenylmethoxy)methyl]-2-furancarbonitrile,
Tetrahydro-2,5-diethyl-5-[(2-fluorophenylmethoxy)-methyl]-2-furancarbonitrile,
Tetrahydro-2,5-diethyl-5-[(2-chlorophenylmethoxy)-methyl]-2-furancarbonitrile,
Tetrahydro-2,5-diethyl-5-[(2-methylphenylmethoxy)methyl]-2-furancarbonitrile,
Tetrahydro-2-methyl-6-ethyl-6-[(2-fluorophenylmethoxy)methyl]-2H-pyran-2-carbonitrile,
Tetrahydro-2-methyl-6-ethyl-6-[(2-pyridinylmethoxy)methyl]-2H-pyran-2-carbonitrile,
Tetrahydro-2,6-diethyl-6-[(2-fluorophenylmethoxy)-methyl]-2H-pyran-2-carbonitrile, as cis/trans mixtures or in the cis or trans isomer form.

The compounds of formula I wherein n is 1 are prepared by a Diels-Alder type reaction of an alkyl vinyl ketone with methyl methacrylate or methyl ethacrylate followed by transesterification of the resulting methyl ester adducts to the n-butyl ester and separation of these esters from the alkyl vinyl ketone dimer. The separated esters are reduced, e.g. with LiAlH4, to the corresponding methanol derivatives. The methanol derivatives are etherified e.g., with RCH2Cl in the presence of NaH, and subsequently treated with HCN to introduce the α-cyano substituent. In a specific example, wherein $R^1$ and $R^2$ are both CH3, the reactants are methyl vinyl ketone and methyl methacrylate.

The compounds of formula I wherein n is 0 are prepared by epoxidation-cyclization of novel cyanohydrins, i.e., 2-hydroxy-5-hexenenitrile or 2,5-dialkyl-2-hydroxy-5-hexenenitrile, of the formula

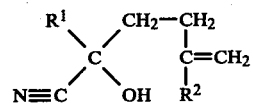

wherein R[1] and R[2] are as defined for formula I, e.g., by epoxidation with m-chloroperbenzoic acid followed by treatment of the resulting epoxy cyanohydrin with hydrochloric acid to yield the novel 2-cyanotetrahydrofuran-5-methanol of the formula

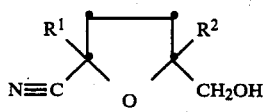

wherein R[1] and R[2] are as defined for formula I, and subsequent etherification e.g., with RCH$_2$Cl. The 2-hydroxy-5-hexenenitriles are prepared by treating the corresponding unsaturated ketone with, acetic anhydride and potassium cyanide by the general procedure of R. Franks, R. Berry, and O. Shotwell, *J. Am. Chem. Soc.*, 71, 3889 (1949). The unsaturated ketones are prepared by (1) reaction of an aldehyde with an unsaturated Grignard reagent followed by selective oxidation of the hydroxy group to a ketone, or (2) reaction of an allyl chloride with an alkanedione as described, for example, in F. Barbot, D. Mesnard, and L. Miginiac, *Organic Preparations and Procedures International* 10, 261 (1978).

The etherification which introduces the group R is conducted by treating the appropriate dihydropyran-methanol derivative or 5-cyanotetrahydrofuranmethanol derivative with a compound of the formula RCH$_2$X in which R is defined as in formula I above and X is a halogen atom, such as bromine, chlorine or iodine, or is a mesyloxy, tosyloxy group or the like, in the presence of a base and an inert diluent. The base is suitably an alkali metal hydride, hydroxide or carbonate, including, for example, sodium hydride, sodium hydroxide, potassium carbonate and the like. Inert diluents are suitably organic solvents, such as ethers, aromatic hydrocarbons, chlorinated hydrocarbons and the like, including, for example, diethyl ether, tetrahydrofuran, dimethyl sulfoxide, toluene, methylene chloride and the like. The reaction can be conducted in a two-phase system, preferably in the presence of a phase-transfer catalyst. For example, the system is aqueous sodium or potassium hydroxide solution with toluene or methylene chloride and the phase-transfer catalyst is an ammonium compound such as tetra-n-butyl-ammonium chloride, bromide, or hydrogen sulfate, triethyl-benzylammonium chloride or the like. The reaction is usually carried out under normal pressures and ambient temperatures. Suitable temperatures for the reaction are from about 0° to about 120° C., preferably from about 20° to about 100° C. The product ethers are recovered and isolated by conventional techniques.

ILLUSTRATIVE EMBODIMENTS

The invention is illustrated by the following embodiments which describe the preparation of typical species of the invention. The embodiments are presented for the purpose of illustration only, and should not be regarded as limiting the invention in any way. The identity of the products, including intermediates, was confirmed by elemental, infrared and nuclear magnetic resonance spectral (NMR) analyses as necessary.

EMBODIMENT 1

3,4-Dihydro-2,6-dimethyl-2H-pyran-2-carboxylic Acid, Butyl Ester

Equimolar amounts of methyl methacrylate (20.0 g) and methyl vinyl ketone (14.0 g) were sealed in a 150 ml stainless steel bomb and kept at 200° C. for two hours. This batch process was repeated several times (1.1 moles total for each reagent). The combined reaction mixture was then distilled to give 55.0 g liquid with bp 42°–52° C. (0.02 torr). By glc the product was a ca 2:1 mixture of the Diels-Alder dimer of methyl vinyl ketone and the methyl ester of the desired adduct. 20.0 g of this mixture was added to 200 ml 1-butanol containing 0.5 g of 50% sodium hydride-mineral oil dispersion. After 35 minutes at ca 25° C. the solvent was stripped, the residue was taken up in pentane, and the organic phase was washed with aqueous sodium bicarbonate and dried over potassium carbonate. After a forerun of the methyl vinyl ketone dimer, careful fractional distillation gave 4.15 g colorless product with bp 62° C. (0.02 torr).

EMBODIMENT 2

3,4-Dihydro-2,6-dimethyl-2H-pyran-2-methanol

A mixture of 3,4-dihydro-2,6-dimethyl-2H-pyran-2-carboxylic acid butyl ester (23.7 g) and lithium aluminum hydride (4.2 g) in 160 ml tetrahydrofuran was heated briefly to reflux and then allowed to cool. After 3.5 hours, excess hydride was destroyed by addition of ethyl acetate (70 ml). Volatile solvents were then stripped, and the residue was treated with 100 ml 15% aqueous sodium hydroxide and extracted with ether. The organic phase was dried over potassium carbonate and distilled to afford 12.3 g colorless product with bp 48°–49° C. (0.03 torr).

EMBODIMENT 3

3,4-Dihydro-2,6-dimethyl-2-[(phenylmethoxy)methyl]-2H-pyran

A mixture of 3,4-dihydro-2,6-dimethyl-2H-pyran-2-methanol (5.8 g) and benzyl chloride (5.2 g) in 50% aqueous sodium hydroxide (16 g) and 10 ml methylene chloride was treated with 0.7 g tetrabutylammonium hydrogen sulfate. After stirring vigorously for 21 hours at room temperature, the mixture was diluted with more methylene chloride and water to facilitate phase separation. The organic phase was separated, washed with water, dried over potassium carbonate and concentrated. Distillation gave 7.6 g colorless liquid with bp 101°–102° C. (0.02 torr).

EMBODIMENT 4

Tetrahydro-2,6-dimethyl-6-[(phenylmethoxy)methyl]-2H-pyran-2-carbonitrile, Mixture of cis (Z) and trans (E) Isomers A mixture of 15.0 g, 3,4-dihydro-2,6-dimethyl-2-[(phenylmethoxy)-methyl]-2H-pyran, 1.75 g liquid hydrogen cyanide, and 0.1 g pyridine sealed in a 30 ml glass bomb was kept at 150° C. for 16 hours. The resulting dark brown solution was distilled (Kugelrohr) to give 15.7 g colorless product, bp 112°–118° C. (0.01 torr), as an isomeric mixture, ca 4:6, cis:trans, based on NMR spectrum in CDCl$_3$.

EMBODIMENT 5

Tetrahydro-2,6-dimethyl-6-[(phenylmethoxy)methyl]-2H-pyran-2-carbonitrile, Cis (Z) Isomer The product of Embodiment 4 was separated into its cis and trans isomeric components on a Waters 500 Preparative HPLC using a silica gel column, 9:1 pentane:ether as eluent, and one recycle. A total of 14.9 g of the product of Embodiment 4 was processed in ca 3 g batches. The purified isomers were isolated as oils, bp not determined, in the amounts of 4.5 g cis (Z) isomer.

EMBODIMENT 6

Tetrahydro-2,6-dimethyl-6-[(phenylmethoxy)methyl]-2H-pyran-2-carbonitrile, Trans (E) Isomer The trans (E) isomer from the above separation in Embodiment 5 was secured in the amount of 8.1 g.

EMBODIMENT 7

5-Methyl-5-hexen-2-one

This substance was prepared from methallyl chloride and 2,4-pentanedione in ethanolic potassium carbonate. The colorless liquid product had bp 67°–72° C. (30 torr).

EMBODIMENT 8

2,5-Dimethyl-2-hydroxy-5-hexenenitrile

Cyanohydrin formation was carried out according to a general literature procedure. Thus, a mixture of 5.60 g 5-methyl-5-hexen-2-one in 10.20 g acetic anhydride was cooled with an ice-bath and treated dropwise with a soution of 6.5 g potassium cyanide in 13 ml water. After stirring overnight at ca 25° C., the mixture was made basic (litmus paper) by addition of saturated sodium carbonate solution. The product was extracted with methylene chloride. The extract was washed with water, dried (MgSO4), and concentrated (rotary evaporator) to give crude liquid cyanohydrin, 7.12 g. This crude product was used directly in the following epoxidation-cyclization step without distillation.

EMBODIMENT 9

Tetrahydro-5-(hydroxymethyl)-2,5-dimethyl-2-furancarbonitrile Mixture of cis (Z) and trans (E) Isomers To a cooled (ice bath) and stirred mixture of 139.52 g 86% m-chloroperbenzoic acid in 2 liters methylene chloride was added 87.98 g of crude 2,5-dimethyl-2-hydroxy-5-hexenenitrile. After 30 minutes at 3° C., the mixture was allowed to warm to room temperature (ca 25° C.). The resulting mixture, which contained the intermediate epoxy cyanohydrin, was then treated with 790 ml of 0.12 N hydrochloric acid to effect cyclization. After stirring vigorously for an additional 2 hours at ca 25° C., the organic phase was separated, washed with 10% aqueous sodium carbonate and dried (MgSO4). Evaporation of solvent and distillation of the residue afforded 62.87 g product with bp 100°–105° C. (0.3 torr).

EMBODIMENT 10

Tetrahydro-2,5-dimethyl-5-[(phenylmethoxy)methyl]-2-furancarbonitrile (cis (Z)-Isomer)

With exclusion of moisture, 0.50 g 50% sodium hydride in mineral oil was added to 1.55 g cis-trans-tetrahydro-5-(hydroxymethyl)2,5-dimethyl-2-furancarbonitrile in 10 ml dry dimethylformamide. Brief warming to 40° C. was required to complete hydrogen evolution. Then the resulting slurry of the sodium alkoxide derivative was cooled to −10° C. and treated with 1.71 g benzyl bromide. After warming to 25° C. for one hour, the mixture was poured onto ice and extracted with pentane. The extract was washed with water, dried (MgSO4), and concentrated. The residue, which was a crude mixture of cis- and trans-isomers of the desired product, was purified and isomerically separated, by preparative hplc (Waters 500 instrument) using a silica gel column and ether:hexane (15:85) as eluent to yield 1.0 g of the cis (Z)-isomer, bp not determined.

EMBODIMENT 11

Tetrahydro-2,5-dimethyl-5-[(phenylmethoxy)methyl-2-furancarbonitrile (Trans (E)-Isomer)

From the separation in Embodiment 10 0.85 g of the trans (E) isomer was obtained, bp not determined.

EMBODIMENT 12

Tetrahydro-2,5-dimethyl-5-[(2-pyridinylmethoxy)methyl]-2-furancarbonitrile (cis (Z)-Isomer)

Freshly liberated 2-picolinyl chloride was secured by extracting a mixture of 1.48 g potassium carbonate and 1.64 g 2-picolinyl chloride in 10 ml water with methylene chloride. The extract was dried (MgSO4) and concentrated (rotary evaporator). To the residue was added 10 ml dry dimethylformamide and the remaining methylene chloride was removed by further evaporation. The resulting solution was then added to a mixture of 10 mmol of the sodium salt of tetrahydro-5-(hydroxymethyl)-2,5-dimethyl-2-furancarbonitrile as a mixture of cis-trans isomers in 10 ml dry dimethylformamide prepared as described in Embodiment 10 above. The reaction progress and workup also followed the procedure for Embodiment 10 with the exception that crude product was secured from both pentane and ether extraction of the ice-quenched mixture. The crude product, which consisted of both cis- and trans-isomers, was purified and isomerically separated by preparative hplc using a silica gel column and ethyl acetate:pentane (60:40) as eluent. The cis (Z)-isomer amounted to 0.69 g bp not determined.

EMBODIMENT 13

Tetrahydro-2,5-dimethyl-5-[(2-pyridinylmethoxy)methyl)]-2-furancarbonitrile (Trans (E)-Isomer)

The trans (E)-isomer from the above hplc separation weighed 0.59 g, bp not determined.

EMBODIMENT 14

1-Chloro-2,2-bis(chloromethyl)butane

To a mixture of 134 g 2,2-bis(hydroxymethyl)butanol, 79.1 g pyridine and 100 ml cyclohexane was added 535 g thionyl chloride with provision for scrubbing evolved acid gases. The mixture was heated at reflux for six hours and then allowed to stand at room temperature over a weekend. After removing volatiles (rotary evaporator), the residue was taken up in methylene chloride and washed once with water and then twice with concentrated sulfuric acid. The solution was dried (magnesium sulfate) and distilled to give 148 g of product with bp 64°–65° C. (0.04 torr).

EMBODIMENT 15

5-Methylene-2-heptanol

A solution of 3-methylenepentyl magnesium chloride was prepared from 56.86 g 1-chloro-2,2-bis(chloromethyl)butane and 14.59 g magnesium with exclusion of moisture ($N_2$) by adding the halide in 60 ml tetrahydrofuran to the metal in 90 ml of the same solvent at such a rate that reflux was maintained. A small amount of iodine and methyl iodide was used to initiate the reaction. The mixture was refluxed for an additional one hour. Then with cooling (dry ice-acetone bath), 44.05 g acetaldehyde in 60 ml tetrahydrofuran was added dropwise at −30° C. After warming to −10° C., the reaction mixture was quenched first with 360 ml water and then 180 ml 15% sulfuric acid, and extracted with methylene chloride. The extract was washed with water and 10% sodium bicarbonate, dried over magnesium sulfate, and distilled. The product weighed 26.80 g, bp 90°–93° C. (30 torr).

EMBODIMENT 16

5-Methylene-2-heptanone

With exclusion of moisture ($N_2$) and cooling (−19° C., carbon tetrachloride-dry ice slush bath), a solution of 19.23 g 5-methylene-2-heptanol in toluene was added to a stirred mixture of 30.04 g N-chlorosuccinimide and 19.10 g dimethyl sulfide in toluene. The mixture was allowed to warm to ca 25° C. over a two-hour period. Then 23.2 g triethylamine was added. After five minutes, the reaction mixture was diluted two-fold with ether. Upon washing with 1% hydrochloric acid and then water, the organic phase was dried (magnesium sulfate) and concentrated. Distillation afforded 6.85 g product with bp 73°–76° C. (20 torr).

EMBODIMENT 17

5-Ethyl-2-hydroxy-2-methyl-5-hexenenitrile

To a cooled (ice-bath) solution of 20 g 5-methylene-2-heptanone in 33.5 g acetic anhydride was added dropwise a solution of 21.3 g potassium cyanide in 40 ml water. After stirring overnight at ca 25° C., the mixture was diluted with excess saturated aqueous sodium carbonate. After extraction with methylene chloride, the organic phase was dried over magnesium sulfate. Removal of solvent (rotary evaporator) gave 20.1 g crude cyanohydrin that was immediately used in the following epoxidation-cyclization step of Embodiment 18.

EMBODIMENT 18

5-Cyano-2-ethyl-5-methyltetrahydro-2-furanmethanol

To a cooled (ice-bath) and stirred mixture of 24.87 g m-chloroperbenzoic acid in 360 ml methylene chloride was added dropwise 20.1 g of the cyanohydrin of Embodiment 17. After addition was completed, the mixture was allowed to warm to room temperature (ca 25° C.) and stand over a weekend with exclusion of moisture ($N_2$). Cyclization of the intermediate epoxy cyanohydrin was then effected by treatment with 150 ml 0.12 N hydrochloric acid. The resulting heterogeneous system was stirred vigorously for 2 hours and then filtered. The organic phase was separated and washed with 10% aqueous sodium bicarbonate. After drying over magnesium sulfate, 12.94 g of liquid product was obtained by Kugelrohr distillation, bp 85°–100° C. (0.3 torr).

EMBODIMENT 19-27

Cyano Ether Derivatives

One molecular equivalent of 5-cyano-2-ethyl-5-methyltetrahydro-2-furanmethanol was converted into the sodium alkoxide derivative by treatment with 1.1 molecular equivalents of sodium hydride in dry dimethylformamide with ice-bath cooling. When hydrogen evolution ceased, 1.1 equivalents of the appropriate benzylic chloride was added. In the case of 2-picolinyl chloride, this substance was freshly liberated from its hydrochloride salt by aqueous neutralization with potassium carbonate and extraction with methylene chloride; rapid removal of this solvent at reduced pressure gave the crude 2-picolinyl chloride which was used immediately. After addition of the appropriate benzylic or 2-picolinyl chloride, the reaction mixture was stirred for 1½ hours at ca 25° C. Then the mixture was diluted with 10 volumes of water and extracted with either pentane or ether. The dried ($MgSO_4$) extract, upon removal of solvent, gave a crude product consisting of geometric isomers of the desired substance and small amounts of the symmetrical dibenzyl ether as a minor byproduct. Purification by preparative hplc (Waters 500 Instrument, silica gel column) using hexane containing 5–15 volume percent ether as eluent gave varying degrees of isomeric separation. In the case of the 2-picolinyl product, hexane with 40 volume percent ethyl acetate was employed.

The cyano ether derivatives prepared are set forth in Table 1.

TABLE 1

5-CYANO ETHER DERIVATIVES

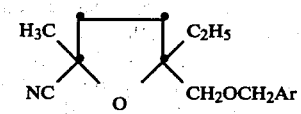

| Embodiment | Ar | Isomer Content[a] (cis:trans) Z:E |
|---|---|---|
| 19 | 2-chlorophenyl | 10:1 |
| 20 | 2-chlorophenyl | 1:1 |
| 21 | 2-methylphenyl | 3:1 |
| 22 | 2-methylphenyl | 1:3 |
| 23 | 2-pyridinyl | not determined |
| 24 | 2-pyridinyl | >10:1 |
| 25 | 2-pyridinyl | >1:10 |
| 26 | 2-fluorophenyl | 1:1 |
| 27 | 2-fluorophenyl | 1:2 |

[a]Estimated by nmr integrations of the —$CH_2OCH_2$— signals.

The invention includes a method of regulating plant growth, including combating unwanted plants, which comprises applying to the locus an effective amount of a compound of Formula I. For example, the compounds can change plant morphology, depress the growth of plants or kill plants. As herbicides, they appear to be more effective when applied preemergence or pre-plant incorporated, particularly to control grassy weeds. For application, the compound generally is applied most effectively by formulating it with a suitable inert carrier or surface active agent, or both. The invention therefore also includes compositions suitable for regulating plant growth, including combating unwanted plants, such compositions comprising an inert carrier or surface-active agent, or both, and as active ingredient at least one compound of formula I.

The term "carrier" as used herein means an inert solid or fluid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground naturally occurring fibrous materials, such as ground corncobs.

Examples of suitable fluid carriers are water; alcohols, such as for example, isopropyl alcohol; glycols; ketones such as for example, acetone, methyl ethyl ketone, methyl isobutyl ketone, isophorone and cyclohexanone; ethers, such as, for example, cellosolves; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquefied normally vaporous gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkyl-aryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25, 50 or 75% by weight of the active compound and usually contain in addition to the solid carrier, 3-10% by weight of a dispersing agent, 15% of a surface-active agent and where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing $\frac{1}{2}$-10% by weight of the active compound. Granules are usually prepared to have a size between 10 and 100 BS mesh (1.676-0.152 mm), and may be manufactured by agglomeration or impregnation techniques. Generally, granules will contain $\frac{1}{2}$-25% by weight of the active compound, 0-1% by weight of additives such as stabilizers, slow release modifiers and binding agents. Emulsifiable concentrates usually contain, in addition to the solvent and, when necessary, cosolvent, 10-50% weight per volume of the active compound, 2-20% weight per volume emulsifiers and 0-20% weight per volume of appropriate additives such as stabilizers, penetrants and corrosion inhibitors. Suspension concentrates are compounded so as to obtain a stable non-sedimenting, flowable product and usually contain 10-75% weight of the active compound, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties, as is appropriate to the intended purpose.

Growth regulator or protection of a locus or area from undesirable plants is effected by applying a compound of Formula I, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in regulating plant growth, including combatting undesired plants, will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kilograms per hectare of the compound of Formula I will be satisfactory.

EXAMPLES OF ACTIVITY WITH RESPECT TO PLANTS

In the following examples, the species of plants that were tested were:

Barnyardgrass (watergrass)—*Enchinochloa crus-galli*

Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf—*Abutilon theophrasti*
Garden cress—*Lepidium sativum*
Johnsongrass—*Sorghum halepense*
Mustard—*Brassica kaber*
Grain sorghum—*Sorghum vulgare* (Pioneer 265)
Corn—*Zea maize* (deKalb X363)
Cotton—*Gossypium hirsutum* (Acala SJ-2)
Soybean—*Glycine max* (Amsoy 71)
Wheat—*Triticum aestivum* (Cajeme 71)
Sugar beet—*Beta vulgaris*
Cocklebur—*Xanthum pennsylvanicum*

Primary Tests—Preemergence Activity

The preemergence (soil) activity of compounds of the invention was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 22 and 2.2 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
|---|---|
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3–4 | Observable damage |
| 1–2 | Plant slightly affected, possibly by the chemical, possibly due to biological variability |
| 0 | No visible effect |

Primary Tests—Postemergence Activity

The postemergence (foliar) activity of compounds of the invention was evaluated by spraying 10-day-old large crabgrass plants, 13-day-old redroot pigweed plants, 6-day-old Johnsongrass plants, 9-day-old velvetleaf plants, 9-day-old yellow foxtail plants and 9-day-old sickle-pod plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days and the effect of the test compound was then evaluated visually, the results being rated on the 0 to 9 scale described above.

Results of the preemergence and postemergence activity tests conducted on the compounds of the invention are set forth in Table I.

TABLE I
HERBICIDAL ACTIVITY

| Embodiment | Preemergence | | | | | | Postemergence | | | | | |
|---|---|---|---|---|---|---|---|---|---|---|---|---|
| | Barnyard-grass | Garden cress | Downy brome | Velvet-leaf | Yellow foxtail | Sickle-pod | Crab-grass | Pig-weed | Johnson-grass | Velvet-leaf | Yellow foxtail | Sickle-pod |
| 5 | 8 | 8 | 7 | 7 | 7 | 3 | 6 | 6 | 0 | 2 | 0 | 2 |
| 6 | 7 | 6 | 6 | 6 | 3 | 3 | 2 | 2 | 0 | 0 | 0 | 2 |
| 11 | 9 | 7 | 9 | 2 | 8 | — | 3 | 0 | 0 | 0 | 0 | 0 |
| 10 | 8 | 8 | 9 | 5 | 8 | — | 2 | 1 | 0 | 0 | 0 | 0 |
| 19 | 8 | 7 | 7 | 6 | 7 | 4 | 7 | 4 | 4 | 3 | 2 | 2 |
| 20 | 9 | 7 | 8 | 7 | 8 | 6 | 8 | 7 | 8 | 5 | 7 | 5 |
| 21 | 9 | 7 | 8 | 7 | 8 | 6 | 8 | 7 | 2 | 4 | 8 | 2 |
| 22 | 9 | 7 | 9 | 7 | 8 | 6 | 8 | 6 | 3 | 3 | 7 | 2 |
| 25 | 9 | 7 | 9 | 6 | 8 | 7 | 3 | 4 | 2 | 3 | 2 | 2 |
| 24 | 9 | 7 | 7 | 7 | 6 | 3 | 2 | 3 | 0 | 2 | 2 | 2 |
| 23 | 9 | 7 | 9 | 5 | 8 | 4 | 2 | 2 | 1 | 5 | 2 | 2 |
| 26 | 9 | 6 | 9 | 5 | 8 | 5 | 7 | 5 | 2 | 4 | 6 | 3 |
| 27 | 9 | 7 | 9 | 5 | 8 | 3 | 8 | 3 | 4 | 4 | 7 | 3 |

I claim:

1. A compound of the formula

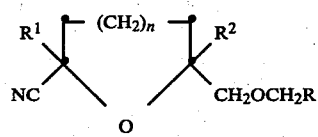

wherein $R^1$ and $R^2$ each independently is a hydrogen atom or an alkyl group containing 1 to 6 carbon atoms; n is 0 or 1; and R is an alkenyl or alkynyl group containing 2 to 4 carbon atoms; a 2-pyridinyl group; a 2-pyridazinyl group; a pyrazinyl group; a pyrimidinyl group, a 2-furanyl group; or a phenyl group optionally substituted by one or more of halogen, cyano, amino, or an alkoxy or alkylthio group containing 1 to 3 carbon atoms each optionally substituted by one or more halogen atoms having an atomic number of 9 or 17, or by an alkyl group containing 1 or 2 carbon atoms optionally substituted by one or more halogen atoms having an atomic number of 9 or 17, hydroxy or alkoxy or alkylthio containing 1 to 2 carbon atoms.

2. A compound according to claim 1 wherein $R^1$ and $R^2$ each independently is an alkyl group containing 1 or 2 carbon atoms.

3. A compound according to claim 2 wherein $R^1$ is a methyl group.

4. A compound according to claim 3 wherein $R^2$ is an ethyl group.

5. A compound according to claim 4 wherein R is an ethynyl group, a 2-pyridinyl group, or a phenyl group optionally substituted by 1 or 2 chlorine or fluorine atoms or methyl groups.

6. A compound according to claim 5 wherein n is 1.

7. A compound according to claim 5 wherein n is 0.

8. A compound according to claim 7 wherein R is 2-chlorophenyl, 2-methylphenyl or 2-fluorophenyl.

9. A plant growth regulating composition comprising an effective amount of a compound according to claim 1 and at least one carrier or surface-active agent.

10. A method of regulating plant growth at a locus comprises applying to the locus or the plants an effective amount of a compound according to claim 1.

* * * * *